USO12142471B2

United States Patent
Kuehl et al.

(10) Patent No.: US 12,142,471 B2
(45) Date of Patent: Nov. 12, 2024

(54) DIRECT AND AUTOMATIC CHROMATOGRAPHY-MASS SPECTRAL ANALYSIS

(71) Applicant: CERNO BIOSCIENCE LLC, Las Vegas, NV (US)

(72) Inventors: Don Kuehl, Windham, NH (US); Stacey Simonoff, Portsmouth, NH (US); Yongdong Wang, Las Vegas, NV (US)

(73) Assignee: CERNO BIOSCIENCE LLC, Las Vegas, NV (US)

( * ) Notice: Subject to any disclaimer, the term of this patent is extended or adjusted under 35 U.S.C. 154(b) by 0 days.

(21) Appl. No.: 18/535,452

(22) Filed: Dec. 11, 2023

(65) Prior Publication Data

US 2024/0136166 A1    Apr. 25, 2024

Related U.S. Application Data

(63) Continuation of application No. PCT/US2023/012187, filed on Feb. 2, 2023.

(60) Provisional application No. 63/305,969, filed on Feb. 2, 2022.

(51) Int. Cl.
*H01J 49/00*    (2006.01)
*G16B 35/10*    (2019.01)

(52) U.S. Cl.
CPC ............ *H01J 49/004* (2013.01); *G16B 35/10* (2019.02)

(58) Field of Classification Search
CPC ................................ H01J 49/004; G16B 35/10
See application file for complete search history.

(56) References Cited

U.S. PATENT DOCUMENTS

2006/0255258 A1    11/2006    Wang
2014/0260536 A1*   9/2014    Sadowski .......... G01N 30/8686
                                                                73/23.37
2014/0297201 A1    10/2014    Knorr
(Continued)

OTHER PUBLICATIONS

International Search Report dated May 15, 2023 for PCT Appl. No. PCT/US2023/12187.

(Continued)

*Primary Examiner* — Manuel L Barbee
(74) *Attorney, Agent, or Firm* — Ohlandt, Greeley and Perle. L.L.P.

(57) ABSTRACT

A method, spectral detection system and computer readable medium for acquiring spectral data for a sample; detecting presence of compounds in a time window; performing a spectral library search using the spectral data from the time window; evaluating the hit list of compounds in each time window and selecting a subset of highly probable compounds; performing a regression analysis between the retention index and the measured retention time for the compounds in the subset; identifying and removing outliers from the subset with large retention index errors; repeating the regression analysis with the outliers removed; calculating the retention index values for all compounds from the entire sample run; comparing the calculated retention index value to that of a possible compound to be identified, and using a retention index match score as an additional metric or filter to additionally assess the likelihood of a possible hit.

26 Claims, 8 Drawing Sheets

(56) References Cited

U.S. PATENT DOCUMENTS

| | | | | |
|---|---|---|---|---|
| 2016/0153945 A1* | 6/2016 | Dessort | ................. | G01N 30/86 73/23.35 |
| 2016/0363569 A1* | 12/2016 | Walsh | ................ | G01N 33/2835 |
| 2020/0232956 A1* | 7/2020 | Kuehl | ................. | H01J 49/0036 |
| 2021/0210317 A1* | 7/2021 | Mistrik | ............... | H01J 49/0036 |

OTHER PUBLICATIONS

Written Opinion Report dated May 15, 2023 for PCT Appl. No. PCT/US2023/12187.

\* cited by examiner

DIRECT AND AUTOMATIC CHROMATOGRAPHY-MASS SPECTRAL ANALYSIS

FIELD OF THE INVENTION

The present invention generally relates to the field of chromatographic separation connected with a spectral detection system such as gas chromatography (GC) with Mass Spectrometry (MS) detection and, more particularly, to methods for acquiring, processing, and analyzing the resulting separation and spectral data.

BACKGROUND OF THE INVENTION

Ervin Kovats (Kováts E., *Helv. Chim. Acta* 41, 1915-1932 (1958)) introduced the use of the chromatography retention time index, called Kovats Retention Index (KRI or simply RI), a dimensionless number sometimes expressed as an index unit or simply "iu", as a method to convert chromatographic retention times (RT) into system-independent constants in gas chromatography (GC). The method depends on a calibration of the chromatograph, usually using a series of n-alkanes, from which the Kovats Index of the n-alkanes is defined as 100 times their carbon number, e.g., n-hexane ($C_6H_{14}$) would be assigned an RI value of 600 iu. Organic compounds can then be assigned an RI value relative to these standards. Models have been developed for both isothermal GC (a log function) runs as well as temperature programmed runs (a linear interpolation function).

RI can be a powerful tool to assist in the unknown identification of organic compounds provided the RI of the unknown compound is available. The widely used NIST/EPA/NIH mass spectral library has updated and maintained a compound database of measured RI values for almost 140,000 compounds (https://www.nist.gov/programs-projects/nist20-updates-nist-tandem-and-electron-ionization-spectral-libraries). In addition, NIST has developed an artificial intelligence (AI) model (see for example, Matyushin, D. D. et al, *Int. J Mol. Sci.* 22(17), 9194 (2021) or Stein, S. E. et al, J. Chem. Inf. Model., 47(3), 975-980 (2007)) which can calculate RI from the chemical structure with high accuracy providing RI values for nearly all of the over 300,000 compounds in the Electron Ionization Mass Spectrometry (EI-MS) database.

While RI values alone cannot necessarily uniquely identify unknow compounds, when coupled with spectral library searching in the ELMS database (e.g., Stein, S. E. et al, *J Amer. Soc. Mass Spectrom.* 5, 859-866 (1994)), a much higher level of confidence of unknown identification can be achieved than by either technique alone. For example, a library search generally produces a list of "best" possible matches of the unknown to the library spectra. However, the list does not usually provide a definitive or unique identification. Likewise, RI does not provide a definitive identification as many compounds can have similar RI values. However, taking together both dimensions of information can improve identification confidence significantly.

To correctly calculate RI values for unknowns one must carefully run a calibration of known compounds, usually an n-alkane ladder, under conditions identical to that of the sample run, which includes flow rate, temperature program, inlet temperature, column, etc. As the RI values will be calculated by interpolation between the RI standards, it is optimal to have the standards spaced evenly and close to each other across the chromatographic run. Any changes in the method or conditions (flow rate, column length, etc.) require re-running the calibration. In addition, over time, the chromatographic conditions may be altered slightly by ambient temperature, column degradation, or just small drifts in the GC electronics and flow controllers, which may require re-calibration. And of course, running a new chromatographic method will require re-running the RI calibration. Thus, the downside of this approach is the additional time and effort to routinely re-run the calibration sample on a regular basis imposing additional burden and leading to reduced throughput and efficiency for the analysis. Another difficulty in using external standards such as n-alkanes is that some alkanes may not elute out of the column before the GC programming is finished, leading to carryovers or other experimental complications, or the alkane standard mix injected does not contain alkanes of high enough alkane numbers to cover the full retention time range of interest.

An internal calibration (introducing known compounds into the run) can also be used to calibrate the GC. This is usually accomplished by adding known compounds into the sample run with known RI values. The advantage of this approach is 1) there is minimal time lapse between the calibration standards and the analytes which minimizes errors due to instrument drift, 2) Internal standards guarantee that the calibration standard and sample are run under identical conditions to maximize accuracy, and 3) it eliminates the need for a separate calibration run and therefore saves time and effort. However, many samples are very complex as is, and adding standards into the sample can further complicate the analysis due to peak co-eluting or ion suppression etc. making it difficult to accurately determine the retention time (RT) of the standards. Finally, it also requires the additional step of making sure that the amount of RI standards added into the sample are comparable to those of analytes contained in the sample itself.

Finally, RI models developed for isothermal (log model) and temperature programmed runs (linear interpolation model) can lead to significant error when applied to runs which combine multiple step temperature ramps or ramps combined with isothermal segments (see example in FIG. 1). Unfortunately, multi-ramp temperature programs are the norm in GC due to their ability to maximize the separation power and minimize the run time. Advanced RI models have been proposed to accurately calculate RI values in such runs, but they require the accurate measurement of three thermodynamic constants $\Delta H$, $\Delta S$, and $\Delta Cp$ for each compound as well as careful characterization of the gas chromatograph (Boswell, P. G. et al, *J. Chromatogr. A.* 1263:179-88 (2012) and Peng B. et al, *J. Chromatogr. A.* 1374:207-215 (2014)). Unfortunately, unlike conventional KRI, these thermodynamic constants are not available for the vast majority of organic compounds. To accurately measure these constants requires running samples containing these compounds under at least three distinctly different temperature programming conditions where all these compounds would elute, a challenging experimental setup and a daunting task, and thus not practical.

Accordingly, it would be desirable and highly advantageous to have methods to overcome the above-described deficiencies and disadvantages of the prior art.

SUMMARY OF THE DISCLOSURE

The present application is directed to the following improvements:
1. A new approach to perform RI calibration without the use of any known standards beforehand, either added to the test sample itself or through an external sample injection or run, saving time and effort while avoiding experimental, lab, or human errors.

2. These RI standards are self-generated and identified through the sample analysis itself using a subset of the analytes from the very same sample.
3. An approach to spectrally select the analytes from a test sample run to be used as RI standards for the calibration of the whole sample run under identical experimental or temperature programming conditions between the standards and analytes from the test sample.
4. An approach to iteratively refine and improve on the set of standards used for RI calibration.
5. Since the RI calibration is internal to the run, it is independent of the separation conditions.
6. The application of calibrated (fitted) or calculated RI value for each detected separation peak to additionally help in its identification, either in the form of an additional metric above and beyond spectral library search or in combination with spectral library search score, which can then be used to color code, in a list of compounds on a computer screen, any identified compounds to indicate the likelihood of correct identification, greatly reducing the burden of the analyst performing the analysis. Such additional identification quality metric provides greater confidence than either spectral identification or RI value identification used alone.
7. Allow for the calculation of RI values retrospectively from runs previously run that did not have traditional RI calibrations to improve the confidence in compound identification.
8. The RI values thus obtained can be added back into an existing spectral library or databases to complement and enhance the RI collection to continuously improve the spectral identification capabilities.
9. While prior art has shown that it is possible to calibrate even a quadrupole MS system for both accurate mass and spectral accuracy and therefore determine the elemental composition of an unknown compound not already contained in a spectral library or database, the RI calculated from its RT can then be compared to the RI predicted from a computer model based on possible chemical structures for the determined elemental composition to determine, select, rank, or screen likely chemical structures.

Each of these aspects will be described below along with experimental results to demonstrate their utilities.

BRIEF DESCRIPTION OF THE DRAWINGS

A component or a feature that is common to more than one drawing is indicated with the same reference number in each of the drawings.

DETAILED DESCRIPTION OF THE PREFERRED EMBODIMENTS

Figure 1:
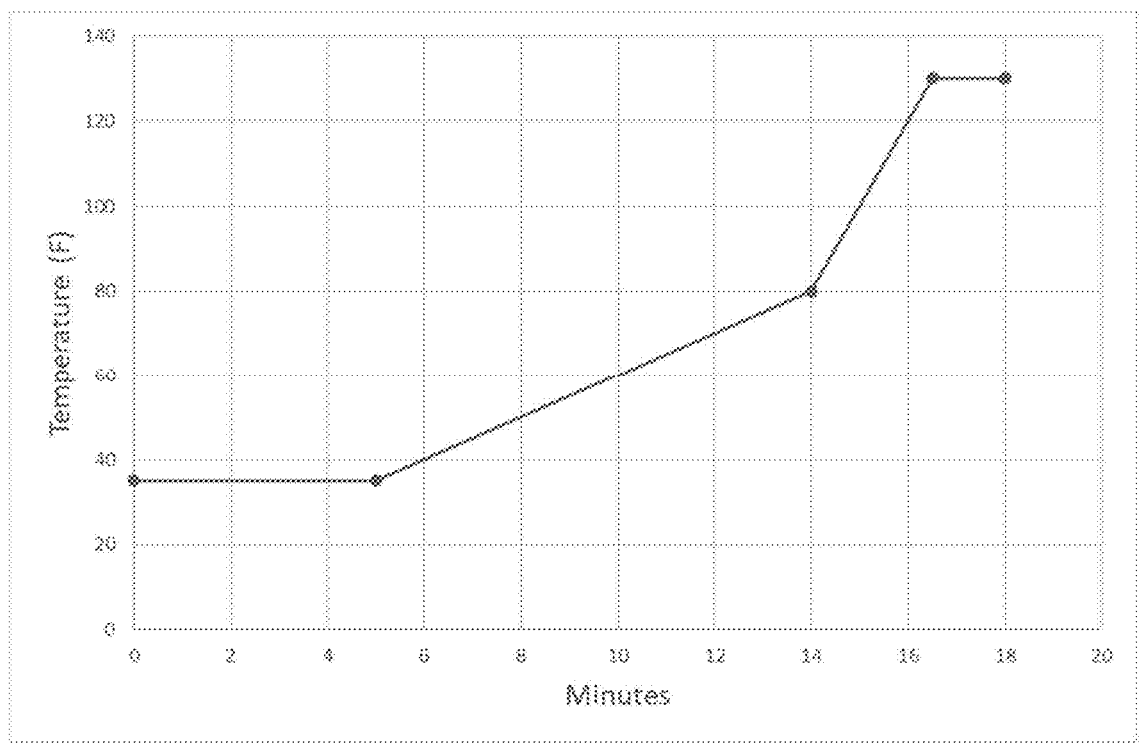
FIG. 1 is an example of a temperature program for GC-MS analysis.
Figure 2:
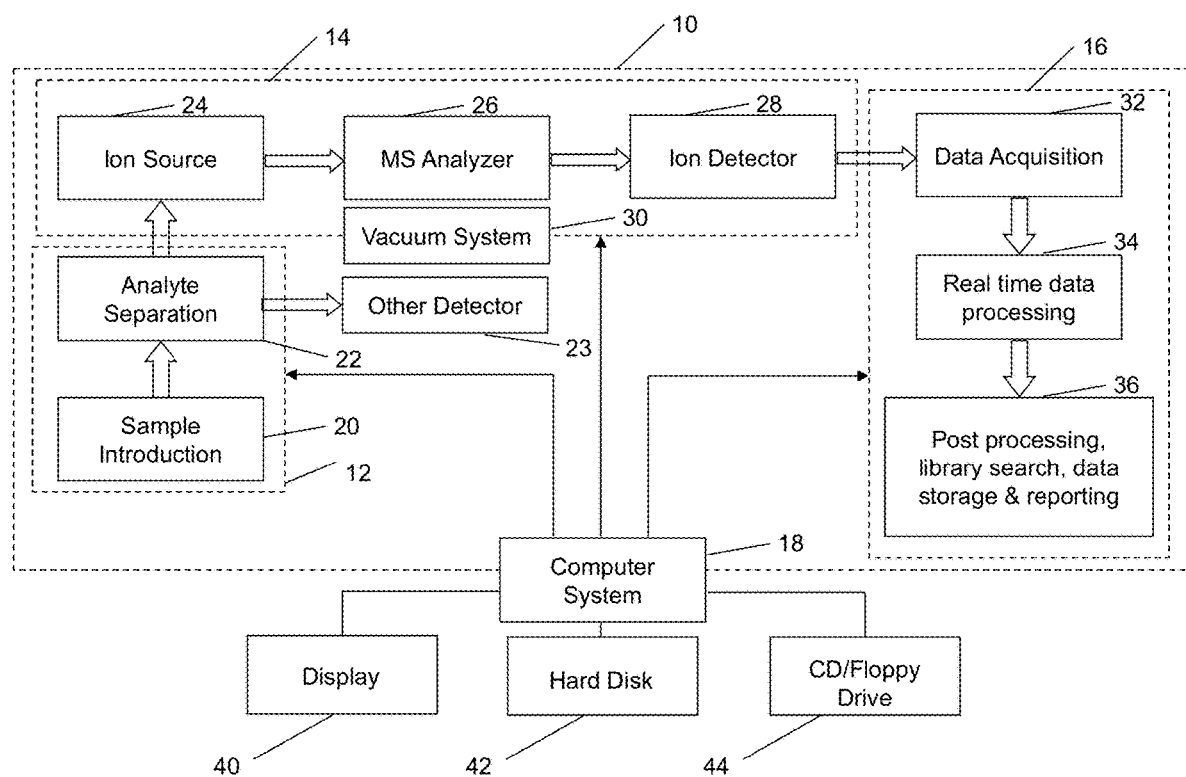
FIG. 2 is a block diagram of a mass spectrometer system coupled to a separation device that can utilize the methods disclosed herein.

Referring to FIG. 2, there is shown a block diagram of an analysis system 10, that may be used to analyze proteins or other molecules, as noted above, incorporating features of the present invention. Although the present invention will be described with reference to the single embodiment shown in the drawings, it should be understood that the present invention can be embodied in many alternate forms or embodiments. In addition, any suitable types of components could be used.

Analysis system 10 has a sample preparation portion 12, other detector portion 23, a mass spectrometer portion 14, a data analysis system 16, and a computer system 18. The sample preparation portion 12 may include a sample introduction unit 20, of the type that introduces a sample containing proteins, peptides, or small molecule drug of interest to system 10, such as LCQ Deca XP Max, manufactured by Thermo Fisher Scientific Corporation of Waltham, MA, USA. The sample preparation portion 12 may also include an analyte separation unit 22, which is used to perform a preliminary separation of analytes, such as the proteins to be analyzed by system 10. Analyte separation unit 22 may be any one of a chromatography column, an electrophoresis separation unit, such as a gel-based separation unit manufactured by Bio-Rad Laboratories, Inc. of Hercules, CA, or other separation apparatus such as ion mobility or pyrolysis etc., as is well known in the art. In electrophoresis, a voltage is applied to the unit to cause the proteins to be separated as a function of one or more variables, such as migration speed through a capillary tube, isoelectric focusing point (Hannesh, S. M., Electrophoresis 21, 1202-1209 (2000), or by mass (one dimensional separation)) or by more than one of these variables such as by isoelectric focusing and by mass. An example of the latter is known as two-dimensional electrophoresis.

The mass spectrometer portion 14 may be a conventional mass spectrometer and may be any one available, but is preferably one of TOF, quadrupole MS, ion trap MS, qTOF, TOF/TOF, or FTMS. If it has an electrospray ionization (ESI) ion source, such ion source may also provide for sample input to the mass spectrometer portion 14. In general, mass spectrometer portion 14 may include an ion source 24, a mass analyzer 26 for separating ions generated by ion source 24 by mass to charge ratio, an ion detector portion 28 for detecting the ions from mass analyzer 26, and a vacuum system 30 for maintaining a sufficient vacuum for mass spectrometer portion 14 to operate most effectively. If mass spectrometer portion 14 is an ion mobility spectrometer, generally no vacuum system is needed and the data generated are typically called a plasmagram instead of a mass spectrum.

In parallel to the mass spectrometer portion 14, there may be another detector portion 23, where a portion of the flow is diverted to for nearly parallel detection of the sample in a split flow arrangement. This other detector portion 23 may be a single channel UV detector, a multi-channel UV spectrometer, or Reflective Index (RI) detector, light scattering detector, radioactivity monitor (RAM) etc. RAM is most widely used in drug metabolism research for $^{14}$C-labeled experiments where the various metabolites can be traced in near real time and correlated to the mass spectral scans.

The data analysis system 16 includes a data acquisition portion 32, which may include one or a series of analog to digital converters (not shown) for converting signals from ion detector portion 28 into digital data. This digital data is provided to a real time data processing portion 34, which processes the digital data through operations such as summing and/or averaging. A post processing portion 36 may be used to do additional processing of the data from real time data processing portion 34, including library searches, data storage and data reporting.

Computer system 18 provides control of sample preparation portion 12, mass spectrometer portion 14, other detector portion 23, and data analysis system 16, in the manner described below. Computer system 18 may have a conventional computer monitor or touch display 40 (or keyboard) to allow for the entry of data on appropriate screen displays, and for the display of the results of the analyses performed. Computer system 18 may be based on any appropriate personal computer, operating for example with a Windows® or UNIX® operating system, or any other appropriate operating system. Computer system 18 will typically have a hard drive 42 or other type of data storage medium, on which the operating system and the program for performing the data analysis described below, is stored. A removable data storage device 44 for accepting a CD, floppy disk, memory stick or other data storage medium is used to load the program on to computer system 18. The program for controlling sample preparation portion 12 and mass spectrometer portion 14 will typically be downloaded as firmware for these portions of system 10. Data analysis system 16 may be a program written to implement the processing steps discussed below, in any of several programming languages such as C++, JAVA or Visual Basic.

It should be noted that for a more general separation with spectral detection system that this disclosure is applicable to, the ion source portion 24 may be replaced by a power source including a light source for optical detection systems or an X-Ray energy source for X-Ray systems. MS analyzer portion 26 may be replaced by a dispersive apparatus such as grating for optical systems with or without fluorescence option, and the ion detector portion 28 may be replaced with the appropriate corresponding light or energy detectors.

Figure 3:
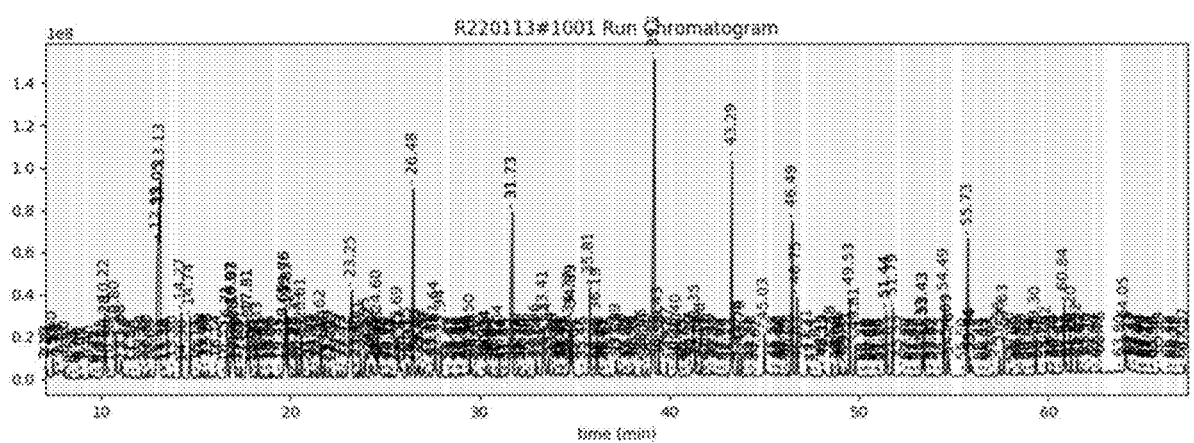
FIG. 3 is a Total Ion Chromatogram (TIC) from the GC/MS analysis of a thermally degraded flavoring sample.

In the preferred embodiment, a sample is acquired through the chromatography/mass spectrometry system described in FIG. 2 with mass spectral data continuously acquired throughout the run, resulting in a data run such as the one shown in FIG. 3, which is an example GC/MS run containing many chromatographic peaks. The detected peaks identified with high confidence through mass spectral library search in the entire sample run are used as the naturally occurring "standards" to calibrate the RI for this entire run or any other run under essentially the same chromatographic or other separation conditions including stationary phases and carrier gas in this case. At least two criteria are used to identify compounds in the run to use as RI calibration standards. The first, the quality of the GC/MS search scores ("match"), is used to tentatively identify each peak. The match values are routinely calculated by comparing the electron impact (EI) ionization fragmentation pattern from the measured mass spectrum to those of pure standards available in EI libraries such as those provided by NIST. The second is the relative retention time of other tentatively identified peaks located before and after the target calibration peak. This can be done in several ways, e.g., by plotting these compounds' known RI values (available from the NIST database as previously obtained values) of the tentatively identified peaks as a function of RT, and performing a least squared fit or regression analysis through all tentatively identified compounds. This process can be used to select a well-spaced subset of reliably identified compounds as internal RI calibration standards to accurately calibrate all the compounds in the whole run for RI. Once calibrated, RI values for all peaks in the run can be assigned to further improve the compound identification above and beyond (NIST) spectral library search alone. The flow of the process is as follows:

a. Automatically detect or otherwise pick all peaks in the chromatogram run and optionally apply mixture deconvolution to identify co-eluting compounds if needed, as disclosed in U.S. provisional patent application Ser. No. 62/632,414, filed on Feb. 19, 2018 and as International Patent Application PCT/US2019/018568 published as WO2019161382.

b. Using the summed, averaged, or deconvoluted mass spectrum within the detected peak's RT window and perform (e.g., NIST/EPA/NIH or simply called NIST) spectral library search to generate a "Hit List" ranked by search/match quality score. While the NIST spectral library is the most widely used publicly available library, there are other similar or specialty libraries that could also be used, e.g., those for forensics or flavor and fragrances etc. Home-grown and proprietary spectral libraries could also be used. Other spectral libraries such as the Sadtler Database of Infrared Spectra widely used in FTIR spectral analysis (http://www.ir-spectra.com/sadtler/sadtler.htm) may also be used.

c. Evaluate each match in the "Hit List" above a specified "good" threshold (e.g., more than 900 score from NIST forward search) and optionally where the difference between forward and the reverse search scores falls within a specified limit (e.g., 30 or 50 from NIST search) to produce a subset of highly probable compounds. For co-elution compounds where a detected chromatographic peak contains a mixture of more than a single compound leading to compromised forward search score due to the presence of spectral interferences, NIST reverse search has been shown to possibly return a very high score due to the masking or elimination of irrelevant m/z values coming from spectral interferences. The search score difference between the forward and reverse search can therefore be used as a good indicator of peak purity here, in the selection of highly probable compounds.

d. Plot and perform a least squares regression between the previously obtained RI of each identified highly probable compound from the above subset vs its RT. Note that a plurality of mathematical/statistical/numerical models may be used as the regression model, including polynomials, splines, probabilistic functions such as logit functions, wavelets such as Poisson wavelet, or a proper combination of these either taken across the entire RT range or for a given RT range. Instead of a certain mathematical or statistical model described above, certain graphical or even purely numerical models (e.g., nearest neighbor clustering, replacement, or averaging etc.) could be used instead. One may also iterate or perform an exhaustive search among these possible models to come up with the best possible model which fits the existing data set well in the least squares or other sense but without overfitting them, i.e., with some residual error on the order of the known retention index measurement error bound of 5-20 iu. When it is possible to linearize, e.g., in the case of polynomials, multiple linear regression (MLR) may be readily applied, using the methodology referenced in U.S. Pat. Nos. 7,577,538 and 6,983,213.

e. Identify "outliers", i.e., compounds whose previously obtained RI values differ significantly from those calculated from the regression model, based on, for example, one or two times the standard deviation cutoff or other statistical measures.

f. Remove outliers from the above subset used for the regression.

g. Repeat the regression analysis with the remaining compounds in the subset until all compounds remaining in the subset are statistically consistent, with a preset number of statistically allowable outliers left.

h. For all compounds contained in the entire run, calculate their RI values from their RT positions using the above regression model.

i. Compare the calculated RI values with the previously obtained RI values from the spectral or other library for tentatively identified compounds based on spectral library search, using RI value match score as an additional metric or filter to additionally assess the likelihood of a possible hit, or combine the RI match value with other metrics including spectral match value into a combined overall search score to more reliably rank the list of tentatively identified compounds, for more confident compound identification. The combination of various match scores may take the form of numerical average after proper normalization or weighting, or the sum of step (or sigmoid) functions where a search score would only be factored in (significantly) if it is above a certain preset threshold.

Figure 4:
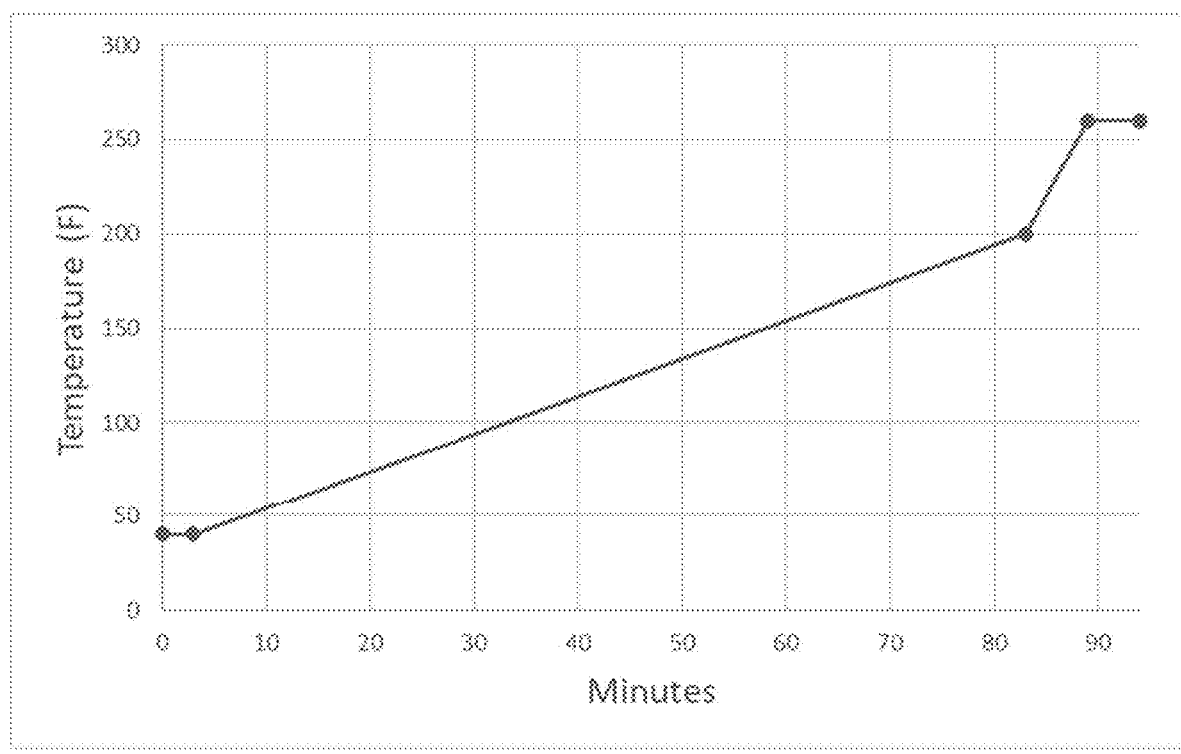
FIG. 4 is the temperature program for GC-MS analysis of a thermally degraded flavoring sample.

Some examples of the process are illustrated in the following figures. FIG. 3 shows a total ion chromatogram (TIC) from a GC/MS analysis of a thermally degraded food flavoring. The sample is complex and contains over 300 compounds as measured by the mass spectrometer. The temperature programming profile is illustrated in FIG. 4 which contains multiple temperature ramps as well as isothermal sections at the beginning and end of the GC run.

Each picked or detected peak in the run is searched against the NIST library in an attempt to identify the corresponding compound. In the algorithms used by NIST, the match score indicates the likelihood of a correct identification. For example, a match value above 900 is considered as excellent indicator of a correct identification. However, it is possible that the top matches are not necessarily the correct matches due to small variations in the spectral patterns arising from experimental or instrumental variations or possible structural/skeletal/positional isomers. However, the top matches are more probably correct.

Figure 5:
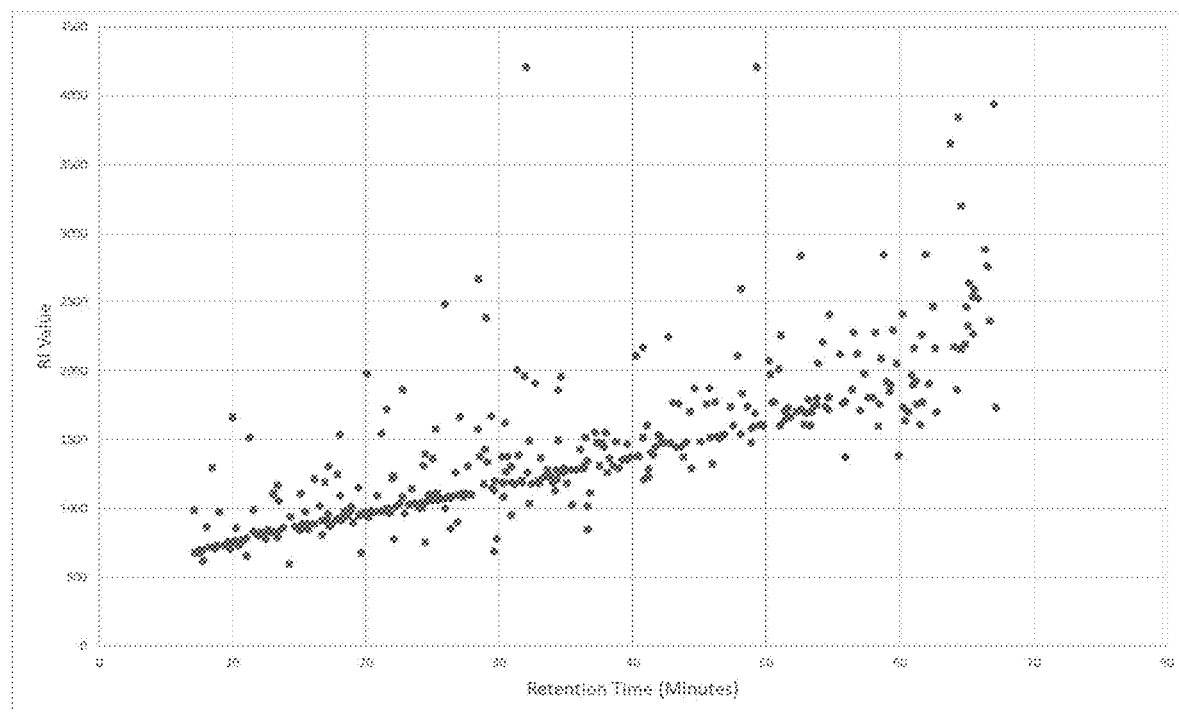
FIG. 5 is a plot of the RI value from the NIST database from the top spectral search hit of each peak vs RT for a thermally degraded flavoring. It is obvious to the eye that there is a nice correlation but also there are many outliers due to miss-identified compounds when using spectral search alone.

Next, the RI data for each top identified compound by match value is read from the database and plotted as a function of GC retention time as shown in FIG. 5. Visually, one can easily recognize a trend in the plot with a large number of outliers in the data. The outliers are either 1) compounds that are not correctly identified by the MS search because the compound is not in the library or 2) the peak is a mixture of coeluting compounds which is misidentified or 3) the signal-to-noise of the compound's spectrum is low making spectral matching poor. These compound outliers are easily eliminated from the plot by evaluating the quality of the match value using spectral search score and/or the difference between forward and reverse search score (an indication of purity).

Figure 6:
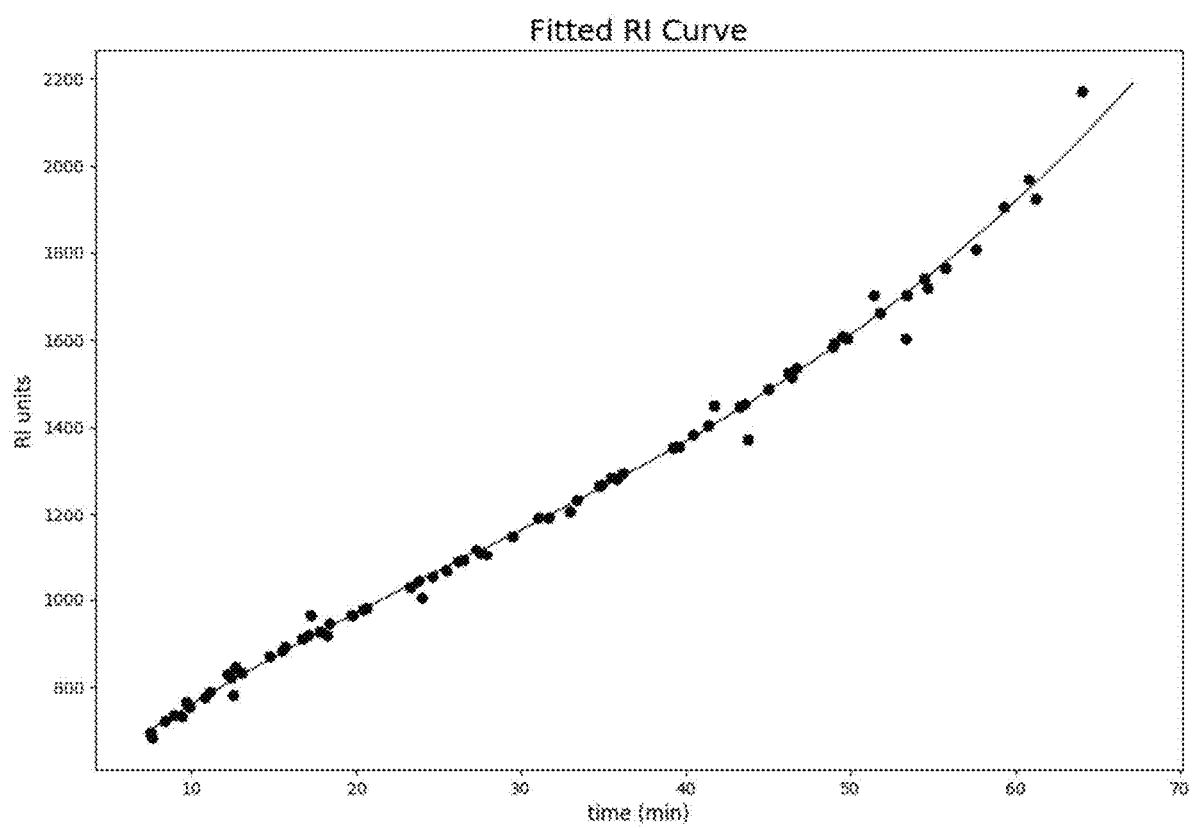
FIG. 6 is a plot of the RI value from the NIST database from the top spectral search hit of each peak vs RT for a thermally degraded flavoring after rejection of all compounds that do not meet the spectral search quality criterion. The final regression line shown (a polynomial in this case) fits the remaining points well with statistically distributed outliers. wherein those located at more than two times the standard deviation away have been excluded from the regression analysis.

Once these outliers are identified and eliminated, the remaining compound RI values can be plotted and fitted to a mathematical/statistical function. As mentioned previously, temperature programming of the GC with multiple temperature ramps causes the retention times to deviate in a non-linear fashion. To accommodate this deviation from classic log or linear Kovats models, the data is fit with a more flexible function, such as a higher order polynomial as shown in FIG. 6.

However, there is still some likelihood that the match values are not always correct. The is especially true for spectrally similar compounds which may have the same chemical formulas but have different chemical structures (known as various forms of isomers in the art). It is well known that while these compounds can be spectrally similar, they can have significantly different RI values. These outliers can be easily identified as having statistically significant deviation from the fitted curve. The outliers can be easily identified from the plot shown in FIG. 5 and can be eliminated by their large deviations from the fitted curve.

With the outliers detected, the process of fitting the data can be repeated to further eliminate outliers if necessary. The number of iterations can be set by reasonable statistical cut-offs, e.g., allowing for 5% of statistical outliers at two times the standard deviation (95% confidence interval under normal distribution). The final fitted curve is the RI calibration that can now be used to assign RI values for every peak and compound in the run given its measured retention time.

Experimental comparison of the RI values generated by this method are found to be as accurate as those using the traditional method of generating RI calibration through the more tedious and time-consuming n-alkane external calibration.

Figure 7:
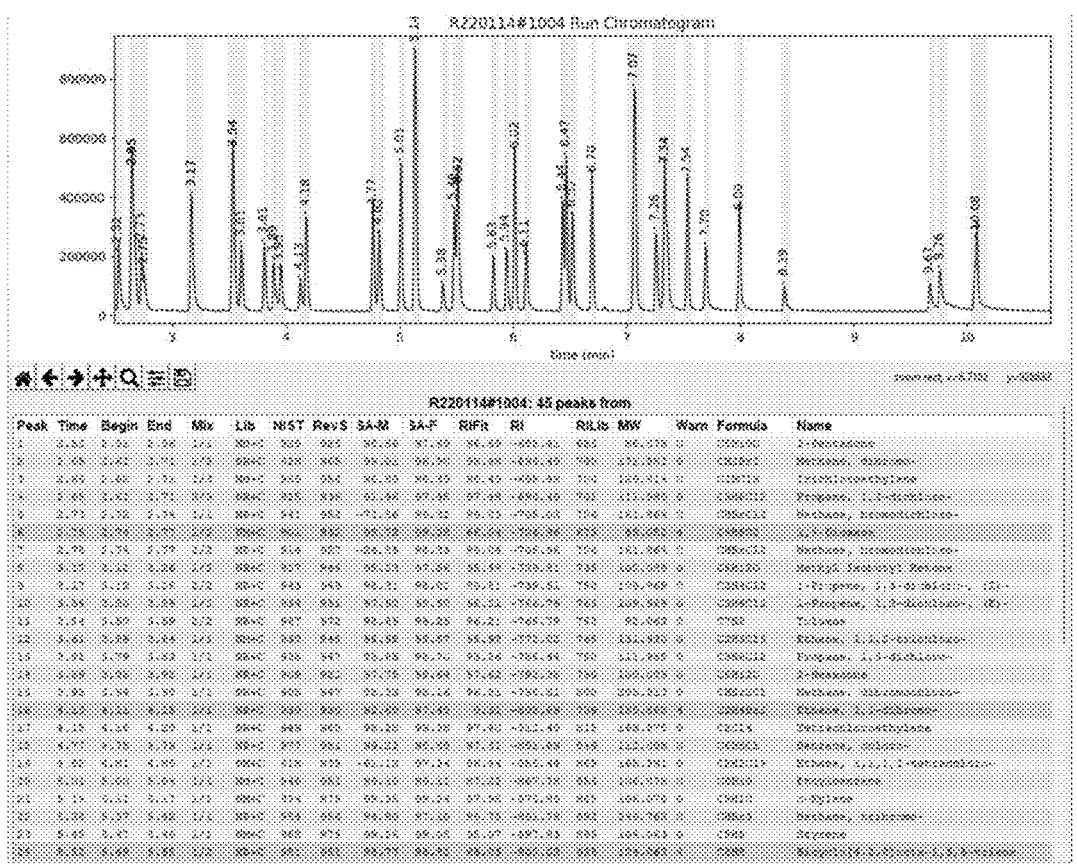
FIG. 7 shows the screen capture for a GC/MS analysis of volatile organic compounds.

FIG. 7 shows the screen capture for a GC/MS analysis of volatile organic compounds. The metrics reported include forward (NIST) and reverse (RevS) library match values, the difference between expected and measured RI values (RIFit where 100 is a perfect match and lesser values indicate relative deviations from the expected) as well as spectral accuracy matching of the compound's molecular ion (SA-M), as disclosed in U.S. Pat. Nos. 6,983,213, 7,493,225 and 7,577,538 and U.S. provisional patent application Ser. No. 62/632,414, filed on Feb. 19, 2018 and as International Patent Application PCT/US2019/018568 published as WO2019161382. The compounds that meet the threshold requirements of all metrics are left without color code, and the ones where one or more of the metrics are below a threshold are highlighted in red. This makes it fast and easy to an analyst to review the data and focus only on "poor" compound identification. Other, intermediate coding colors can also be used to indicate "marginal" identifications.

Figure 8:
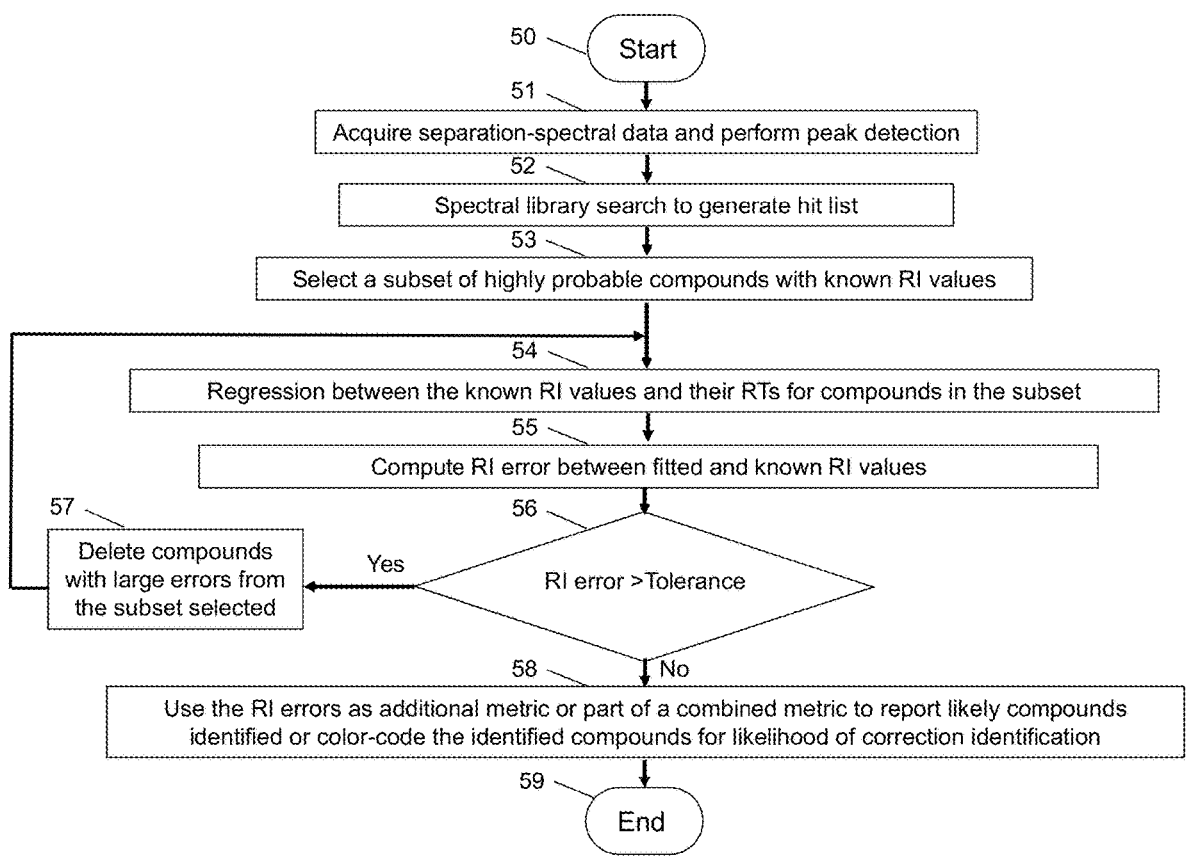
FIG. 8 includes a flow chart of one embodiment disclosed herein.

FIG. 8 shows the above steps in a flow chart of the first embodiment described herein where at 51, spectral data is acquired during the analyte separation process so that separated peaks can be detected. At 52 a time window is selected corresponding to a detected peak with the spectral data combined or averaged in the retention time window for search in a spectral library for a possible list of compounds (hit list). At 53, high quality or confidence hits from the entire run, including all detected peaks, are selected to form a subset of compounds having RI values that have been obtained previously, either stored in a spectral library along with the spectral data or in a separate database separate from the spectral data. At 54, regression analysis is performed between the known RI values and their respective RT positions measured for those compounds in the subset. At 55, an RI error is computed between the fitted RI value from the regression model and the known RI values previously available from the spectral search. At 56, compounds with RI errors larger than a preset tolerance or threshold are indicated. At 57, these compounds with large RI errors are then removed from the subset of compounds before the regression is repeated, until the majority (e.g., 95%) of the compounds in the subset have their RI errors below the tolerance. At 58, the RI error computed for any peak in the entire run is used as an additional metric, or as part of an overall metric including spectral search score, to rank the likely hits for each peak detected, or to color-code a possible compound indicating the likelihood of correct identification.

Although the description above contains many specifics, these should not be construed as limiting the scope of the invention but as merely providing illustrations of some feasible embodiments. For example, the regression model built from one sample run, where appropriate due to the high reproducibility of a given GC/MS system, may be applied to another sample run under substantially the same separation conditions in its entirety, or only partially by adding additionally identified highly probable compounds from a future run into the subset created from a prior run, to dynamically enhance and improve the regression model over all multiple runs or over time. Additionally, the calculated RI values from a sample run may be of a good enough accuracy to be added into a spectral library or database where such values are either missing or less accurate. Furthermore, sometimes a compound in question from a sample run is a true unknown not already contained in a spectral library or database, into which the measured spectral data and the calculated RI value may be added to enhance, augment, or create a new spectral library or database. There are certain advantages in acquiring the spectral data in the raw profile mode and calibrating the profile mode spectral data for mass accuracy and spectral accuracy, as disclosed in U.S. Pat. Nos. 7,577,538 and 6,983,213, for the creation, augmentation, or utilization of accurate profile mode spectral data and library, as disclosed in the U.S. provisional patent application Ser. No. 62/830,832, filed on Apr. 8, 2019 and as U.S. patent application Ser. No. 16/843,505 published as US 2020-0232956 A1. Finally, it is possible to determine the elemental composition of an unknown compound not already contained in a library, even using a conventional quadrupole mass spectrometer, as disclosed in U.S. Pat. Nos. 7,577,538 and 6,983,213. For an unknown compound with its elemental composition and RI value thus determined, one could search for possible chemical structures, using either chemistry knowledge or databases such as ChemSpider (www.chemspider.com). Using the artificial intelligence (AI) model referenced earlier (Matyushin, D. D. et al, *Int. J Mol. Sci.* 22(17), 9194 (2021) or Stein, S. E. et al, *J. Chem. Inf. Model.*, 47(3), 975-980 (2007)), one can predict an RI value for each possible chemical structure and then compare the predicted RI to the calculated RI from the sample run to judge the likelihood that a certain given structure may or may not be the correct hit, potentially providing a turn-key answer machine to the ultimate chemistry problem of what the compound is, through a single GC/MS experiment.

Thus the scope of the disclosure should be determined by the appended claims and their legal equivalents, rather than by the examples given. Although the present disclosure has been described with reference to the embodiments described, it should be understood that it can be embodied in many alternate forms of embodiments. In addition, any suitable size, shape or type of elements or materials could be used. Accordingly, the present description is intended to embrace all such alternatives, modifications and variances which fall within the scope of the appended claims.

It will be understood that the disclosure may be embodied in a computer readable non-transitory storage medium storing instructions of a computer program which when executed by a computer system results in performance of steps of the method described herein. Such storage media may include any of those mentioned in the description above.

The techniques described herein are exemplary, and should not be construed as implying any particular limitation on the present disclosure. It should be understood that various alternatives, combinations and modifications could be devised by those skilled in the art. For example, steps associated with the processes described herein can be performed in any order, unless otherwise specified or dictated by the steps themselves. The present disclosure is intended to embrace all such alternatives, modifications and variances that fall within the scope of the appended claims.

The terms "comprises" or "comprising" are to be interpreted as specifying the presence of the stated features, integers, steps or components, but not precluding the presence of one or more other features, integers, steps or components or groups thereof.

What is claimed is:

1. A method for the analysis of compounds of interest through separation over time when using a mass spectral detection system and making a determination of retention index values, comprising the steps of
   a. acquiring, at a plurality of times, mass spectral data throughout a range of mass to charge ratio for ionized particles of a sample;
   b. selecting a relevant retention time window for presence of possible compounds of interest;
   c. using the acquired mass spectral data in said relevant retention time window to perform a mass spectral library search for compounds in a mass spectral library and identify possible compounds along with their retention index values;
   d. performing a regression analysis, using a regression model, between the retention index values of said possible compounds and their retention times by using a subset of compounds identified;
   e. using said regression model to calculate a retention index value based on the measured retention time for a compound; and
   f. using said calculated retention index value for one of comparing to previously measured retention index value of a known candidate compound to evaluate the likelihood of its correct identification and comparing to predicted retention index value of a previously unknown compound to evaluate the likelihood of a given possible structure.

2. The method of claim 1, where the technique for separation is one of gas chromatography (GC), liquid chromatography (LC), supercritical fluid chromatography, ion chromatography (IC), capillary electrophoresis (CE), gel electrophoresis, ion mobility, and pyrolysis.

3. The method of claim 1, where the spectral detection system is one of a sector mass spectrometer, quadrupole mass spectrometer, Time-of-Flight (TOF) mass spectrometer, Orbitrap mass spectrometer, and Fourier-transform ion cyclotron resonance (FT ICR) mass spectrometer.

4. The method of claim 1, where the retention time includes one of chromatographic retention time, elution time, drift time, and separation time.

5. The method of claim 1, where the retention index values have been previously obtained from measured retention times through the use of calibration standards related to n-alkane for gas chromatography.

6. The method of claim 1, where the regression model is one of a polynomial of a given order, a spline function of a given order, a probabilistic function of a given form, a wavelet of certain form, a graphical model, a numerical model, and a combination of these segmented over a given retention time window.

7. The method of claim 1, where the subset is selected based on spectral library search quality above a given quality threshold.

8. The method of claim 1, where the subset is selected based on one of a difference between and combination of forward and reverse spectral search.

9. The method of claim 1, where the regression model is refined by iteratively excluding from the subset those compounds whose calculated retention index values differs significantly from previously obtained retention index values.

10. The method of claim 1, where the regression model is refined by evaluating and selecting from at least one of mathematical, statistical, graphical, and numerical models.

11. The method of claim 1, where the said regression model is enhanced by other sample runs under substantially the same separation conditions through inclusion of the additionally identified compounds to an existing subset.

12. The method of claim 1, wherein the calculated retention index values are compared to previously obtained retention index values for possible compounds identified through said mass spectral library search.

13. The method of claim 1, wherein a difference between the calculated and previously obtained retention index value is used as one of an additional metric, and combined with other metrics, to perform one of filtering or ranking the possible compounds found.

14. The method of claim 13, wherein one of the other metrics includes a spectral library search score.

15. The method of claim 1, where one of a difference between the calculated and previously obtained retention index and a combined search metric factoring in such difference is used to color-code the compounds on a hit list of compounds on a display where a certain color indicates a certain likelihood of a correct identification.

16. The method of claim 1, where the regression model is applied to one of the same acquisition and a separate subsequent acquisition under substantially the same separation conditions to calculate the retention index of a compound from its retention time.

17. The method of claim 1, where the regression analysis is a multiple linear regression using of one of matrix computation, matrix inversion, singular value decomposition, principal component analysis, and partial least squares.

18. The method of claim 1, where the retention index values calculated for new or additional compounds are added to an existing library or database.

19. The method of claim 1, wherein the spectral data has been acquired in profile mode and the subset of compounds are used to one of create and add to a profile mode mass spectral library.

20. The method of claim 1, wherein the spectral data acquired has been calibrated for one of mass accuracy and spectral accuracy for elemental composition determination of an unknown compound not already contained in said mass spectral library.

21. The method of claim 1, wherein the calculated retention index is compared to retention indexes predicted by computer from possible chemical structures for a given elemental composition to aid in one of determination, selection, ranking, and screening of likely structures of a compound not already in the mass spectral library.

22. A spectral detection system including a mass spectrometer operating in accordance with the method of claim 1.

23. For use with a computer associated with a spectral detection system including a mass spectrometer, a non-transitory computer readable medium having computer readable program instructions readable by the computer for causing the spectral detection system to operate in accordance with the method of claim 1.

24. The method of claim 1, wherein the mass spectral library includes a database of 140,000 or more compounds.

25. The method of claim 1, further comprising retrospectively calculating retention index values from prior runs that did not have retention index calibration.

26. The method of claim 1, further comprising adding determined retention index values to a mass spectral library.

* * * * *